(12) United States Patent
Ueda et al.

(10) Patent No.: US 10,174,174 B2
(45) Date of Patent: Jan. 8, 2019

(54) WATER-ABSORBING RESIN PARTICLES, ABSORBER COMPRISING SAME, AND ABSORBENT ARTICLE

(71) Applicant: SDP Global Co., Ltd., Tokyo (JP)

(72) Inventors: Yusuke Ueda, Tokyo (JP); Kazuhiro Takahashi, Tokyo (JP); Lanxian Chen, Tokyo (JP)

(73) Assignee: SDP Global Co., Ltd., Tokyo (JP)

( * ) Notice: Subject to any disclaimer, the term of this patent is extended or adjusted under 35 U.S.C. 154(b) by 0 days.

(21) Appl. No.: 15/313,148

(22) PCT Filed: May 22, 2015

(86) PCT No.: PCT/JP2015/064741
§ 371 (c)(1),
(2) Date: Nov. 22, 2016

(87) PCT Pub. No.: WO2015/178481
PCT Pub. Date: Nov. 26, 2015

(65) Prior Publication Data
US 2017/0190847 A1 Jul. 6, 2017

(30) Foreign Application Priority Data

May 23, 2014 (JP) ................................. 2014-107002
May 23, 2014 (JP) ................................. 2014-107016

(51) Int. Cl.
| | | |
|---|---|---|
| A61L 15/60 | (2006.01) | |
| C08G 81/02 | (2006.01) | |
| C08J 3/12 | (2006.01) | |
| D06M 15/263 | (2006.01) | |
| D06M 15/59 | (2006.01) | |
| D06M 23/08 | (2006.01) | |
| A61L 15/58 | (2006.01) | |
| C08F 8/46 | (2006.01) | |

(52) U.S. Cl.
CPC .............. *C08J 3/126* (2013.01); *A61L 15/58* (2013.01); *A61L 15/60* (2013.01); *C08F 8/46* (2013.01); *C08G 81/02* (2013.01); *D06M 15/263* (2013.01); *D06M 15/59* (2013.01); *D06M 23/08* (2013.01); *C08J 2300/14* (2013.01); *C08J 2333/02* (2013.01); *C08J 2453/00* (2013.01); *C08L 2207/53* (2013.01)

(58) Field of Classification Search
None
See application file for complete search history.

(56) References Cited

U.S. PATENT DOCUMENTS

| | | | | |
|---|---|---|---|---|
| 6,090,875 A | * | 7/2000 | Staples | C08J 3/124 524/313 |
| 2006/0178071 A1 | * | 8/2006 | Schmidt | A61L 15/26 442/417 |
| 2007/0135554 A1 | * | 6/2007 | McIntosh | C08L 51/06 524/492 |
| 2008/0021130 A1 | * | 1/2008 | McIntosh | C08L 51/06 523/111 |
| 2011/0319847 A1 | | 12/2011 | McKiernan et al. | |

FOREIGN PATENT DOCUMENTS

| | | |
|---|---|---|
| CN | 1337977 A | 2/2002 |
| CN | 101326234 A | 12/2008 |
| EP | 0530231 A1 | 3/1993 |
| EP | 1162226 A1 | 12/2001 |
| EP | 1969053 B1 | 5/2014 |
| JP | 05-507511 A | 10/1993 |
| JP | 06-245958 A | 9/1994 |
| JP | 06-248187 A | 9/1994 |
| JP | 2000-212458 A | 8/2000 |
| JP | 2008-538081 A | 10/2008 |
| JP | 2009-519356 A | 5/2009 |
| JP | 2010-116548 A | 5/2010 |
| JP | 2012-219231 A | 11/2012 |
| KR | 20170005491 A | 1/2017 |
| WO | 91/18042 A1 | 11/1991 |

OTHER PUBLICATIONS

Bynel Resin Product Data Sheet, Dupont, pp. 1-4, Aug. 25, 2014 (Year: 2014).*
Office Action dated Feb. 2, 2018, issued for the Japanese patent application No. 2016-521161 and English translation thereof.
Office Action dated May 9, 2017, issued for the Korean patent application No. 10-2016-7036024 and English translation thereof.
First Office Action issued in corresponding Chinese Patent Application No. CN201580027096.3, dated Jul. 4, 2018.

(Continued)

*Primary Examiner* — Peter A Salamon
(74) *Attorney, Agent, or Firm* — Locke Lord LLP; James E. Armstrong, IV; Nicholas J. DiCeglie, Jr.

(57) ABSTRACT

Provided are the following: water-absorbing resin particles with which an absorber can be manufactured, the absorber enabling ample anchoring to be obtained without compromising on water absorbency; and an absorber obtained by anchoring together the water-absorbing resin particles and a fibrous base material. The present invention is: core-shell water-absorbing resin particles constituted of a core layer (P) containing a water-absorbing resin (A) and a shell layer (Q), the shell layer (Q) containing a thermoplastic resin (B) having a melting point of 50 to 180° C., and the thermoplastic resin (B) being a polymer having a hydrophobic block comprising a polyolefin; an absorber obtained by anchoring the water-absorbing resin particles to a fibrous base material (F); and an absorbent article made using such absorber.

13 Claims, No Drawings

(56) References Cited

OTHER PUBLICATIONS

Search Report issued in corresponding Chinese Patent Application No. CN 2015800270963, dated Jul. 4, 2018.
Supplementary European Search Report dated Nov. 13, 2017, issued for the European patent application No. 15795426.4.
International Search Report dated Aug. 4, 2015, issued for PCT/JP2015/064741.

* cited by examiner

WATER-ABSORBING RESIN PARTICLES, ABSORBER COMPRISING SAME, AND ABSORBENT ARTICLE

TECHNICAL FIELD

The present invention relates to a water-absorbing resin particle, and to an absorber and an absorbent article using the same.

BACKGROUND ART

Absorbent articles (disposable diapers, etc.) using water-absorbing resin particles are usually produced by fixing water-absorbing resin to a matrix composed of cellulose fibers uniformly and packing them with organic synthetic fiber such as non-woven fabric. In practical use, however, water-absorbing resin particles are shed or moved easily by vibration to generate deviation of particles in absorbers. As a result, efficient diffusion of an absorbate such as urine is disturbed, so that such problems as urine leakage and developing a rash have been caused.

In recent years, needs for reduction in thickness of absorbent articles such as disposable diapers have continued to evolve and the trend toward pulp-free has increasingly been advancing. That is, the ratio of the pulp serving as a matrix in the absorber relative to the water-absorbing resin particles has become less than before, and therefore the fixation of water-absorbing resin particles in an absorber has become more difficult and, for example, such problems as urine leakage and developing a rash tend to occur more easily than before. From such a point of view, there has been demanded a technology to fix water-absorbing resin particles to pulp fiber or other fibrous base materials efficiently.

As attempts for solving the above problems, there are known (1) a method in which a pressure-sensitive adhesive is applied to the surface of a fibrous base material and then water-absorbing resin particles are adhered, and (2) a method in which water-absorbing resin particles are dispersed in an organic solvent in which a binder has been dissolved, then the dispersion is applied to or included in a fibrous base material, followed by heating and drying, thereby vaporizing the organic solvent and achieving fixation. However, the method (1) has a problem that deterioration in absorber performance or handling nature are invited because the fibrous base material itself is adhered by a pressure-sensitive adhesive which does not take part in adhesion between the water-absorbing resin particles and the fibrous base material. In the method (2), the process of heating, drying and vaporizing the organic solvent is complicated and requires increased costs and there is an apprehension regarding the safety of residual organic solvent.

In addition, a new method known in the art is a method of fixing water-absorbing resin particles to a fibrous base material by coating the surface of the water-absorbing resin particles beforehand with heat-weldable resin such as polyolefin resin, e.g., polyethylene wax, polyolefin derivatives modified with acid anhydrides or the like, polyester resin, polyamide resin, and polystyrene resin, or by mixing such heat-weldable resin with water-absorbing resin particles and then heat-welding them.

PRIOR ART DOCUMENTS

Patent Documents

Patent Document 1: JP-A-6-245958

SUMMARY OF THE INVENTION

Problems to be Solved by the Invention

However, since a heat-weldable resin as described above is not sufficient in amphipathicity though it is high in affinity with one of a hydrophilic water-absorbing resin particle having a polar group or a hydrophobic fibrous base material, it is low in fixability and addition thereof in an amount of 5% by weight or more is required in order to obtain sufficient fixability. However, this case is not favorable because the water absorption property, which is a property inherent to a water-absorbing resin particle, may be greatly impaired.

The present invention is to provide a water-absorbing resin particle from which there can be produced an absorber with which a sufficient fixability can be obtained without imparting the water absorbing property, which is a property inherent to a water-absorbing resin particle, and which does not induce problems such as those described above, an absorber in which the water-absorbing resin particle is fixed to a fibrous base material, and an absorbent article using the absorber.

Solutions to the Problems

The present inventors studied earnestly in order to attain the above-mentioned object, and as a result, have accomplished the present invention by finding that a water-absorbing resin particle having a certain composition can solve the above-described problem. That is, the present invention includes a core-shell type water-absorbing resin particle composed of a core layer (P) and a shell layer (Q), wherein the (P) comprises a water-absorbing resin (A), the (Q) comprises a thermoplastic resin (B) having a melting point of 50 to 180° C., and the thermoplastic resin (B) is a polymer having a hydrophobic block comprising a polyolefin; an absorber in which the aforesaid water-absorbing resin particle is fixed to a fibrous base material (F); and an absorbent article using the aforesaid absorber.

Advantages of the Invention

An absorber in which an absorbing resin particle of the present invention is fixed on a fibrous base material excels in fixability to the fibrous base material while maintaining excellent water absorbing performance and exhibits excellent shape retention property even after being swollen.

MODE FOR CARRYING OUT THE INVENTION

In the core-shell type water-absorbing resin particle of the present invention, the core layer (P) comprises the water-absorbing resin (A). While the core layer (P) may be constituted of substantially only the water-absorbing resin (A), it may contain other additives for resin described below in a known loading. The water-absorbing resin (A) is not particularly limited and examples thereof include a water-absorbing resin that is a hydrophilic crosslinked polymer usually having an ability to absorb water in an amount of about 30 times to 1000 times its own weight and having a hydrophilic group in its constitutional unit such as a carboxylic acid (salt) group [referring to a carboxylic acid and/or a carboxylic acid salt; hereinafter the same expression is used], a sulfonic acid (salt) group, a phosphoric acid (salt) group, a tertiary amino group, a quaternary ammonium salt group, a hydroxyl group, and polyethylene oxide group, and the type and the production method of the resin is not particularly limited. Examples of a water-absorbing resin (A) that can be used suitably for the present invention include the starch-acrylic acid (acid) copolymers disclosed in JP-B-53-46199, JP-B-53-46200, etc., a crosslinked or self-crosslinked polyacrylic acid (salt) prepared by the reverse phase suspension polymerization method disclosed in JP-B-54-30710, JP-B-56-26909, etc., a crosslinked polyacrylic acid (salt) obtainable by the aqueous solution polymerization (adiabatic polymerization, thin film polymerization, spray polymerization, etc.) disclosed in JP-A-55-133413, etc., a saponified copolymer of a vinyl ester with an unsaturated carboxylic acid or a derivative thereof disclosed in JP-A-52-14689, JP-A-52-27455, etc., a sulfonic acid (salt) group-containing water-absorbing resin disclosed in JP-A-58-2312, JP-A-61-36309, etc., a crosslinked isobutylene-maleic anhydride copolymer, a hydrolysate of a starch-acrylonitrile copolymer, a crosslinked carboxymethyl derivative, a crosslinked polyethylene oxide derivative, a crosslinked polyvinyl alcohol derivative, and a partial hydrolysate of polyacrylamide.

Moreover, water-absorbing resins obtained by further surface-crosslinking the above water-absorbing resins.

Two or more of the above water-absorbing resins may be used in combination.

The absorbing power of the water-absorbing resin (A) for a physiological saline solution (aqueous 0.9% sodium chloride solution) is preferably 30 or more times, more preferably 35 to 100 times, even more preferably 40 to 80 times its own weight.

In the core-shell type water-absorbing resin particle of the present invention, the shell layer (Q) layer contains a thermoplastic resin having a melting point of 50 to 180° C. (B) (hereinafter also refers to as thermoplastic resin (B) or simply as (B)). The melting point of the (B) is preferably 60 to 160° C. When the melting point is lower than 50° C., a problem of blocking occurs during storage or during use. On the other hand, if the melting point exceeds 180° C., treatment must be performed at a high temperature when fixing the water-absorbing resin particle to the fibrous base material (F), and this requires a large quantity of heat energy and therefore is not economical, and moreover, treatment at a high temperature causes deterioration in absorption performance or staining phenomenon. While the shell layer (Q) layer may be constituted of substantially only the thermoplastic resin (B), it may contain other additives for resin described below in a known loading. It is noted that when a low molecular weight polyolefin (H) and/or a plasticizer (I) described below, etc. is/are used, the (Q) contains these ingredients as well.

The thermoplastic resin (B) is a polymer having a hydrophobic block comprising a polyolefin, and a block copolymer having a hydrophobic block comprising a polyolefin can be used, for example.

The thermoplastic resin constituting the polymer has a melting point of 50 to 180° C., and examples thereof include polyolefin resins (polyethylene, polypropylene, low molecular weight polyethylene, low molecular weight polypropylene, etc.), polyolefin derivatives (maleic acid-modified polyethylene, chlorinated polyethylene, maleic acid-modified polypropylene), polyester resins, polyamide resins, polycaprolactone resins, polystyrene resin and its derivatives (polystyrene, sulfonated polystyrene, styrene-maleic anhydride copolymers, etc.), thermoplastic polyurethane resins, high molecular weight polyethylene glycol, polyvinyl acetate resins, waxes (paraffin wax, bees wax, beef tallow, etc.), long chain fatty acid ester resins, and mixtures of two or more of these. Of these, resins other than polyolefin and derivatives thereof can constitute a part other than the hydrophobic block comprising a polyolefin.

As the polyolefin that constitutes the hydrophobic block possessed by the thermoplastic resin (B) (hereinafter also referred to as polyolefin (a)), there can preferably be used a polyolefin having carbonyl groups (preferably, carboxyl groups; the same applies hereinafter) on both ends of the polymer (a1), a polyolefin having hydroxyl groups on both ends of the polymer (a2), and a polyolefin having amino groups on both ends of the polymer (a3), and moreover, a polyolefin having a carbonyl group on one end of the polymer (a4), a polyolefin having a hydroxyl group on one end of the polymer (a5), and a polyolefin having an amino group on one end of the polymer (a6) can be used. Of these, the polyolefins (a1) and (a4), which have carbonyl groups, are more preferred because of their ease to be modified.

Examples of the (a1) include one prepared by introducing carbonyl groups to both ends of a polyolefin (a0) comprising a polyolefin capable of being modified on its both ends preferably as a main ingredient (in a content of 50% by weight or more, more preferably 75% by weight or more, particularly preferably 80 to 100% by weight). The (a0) is usually a mixture of a polyolefin both ends of which can be modified, a polyolefin one end of which can be modified, and a polyolefin having not end groups capable of being modified and preferably is one the main ingredient of which is a polyolefin both ends of which can be modified.

A polyolefin obtainable by (co)polymerization (meaning homopolymerization or copolymerization; the same applies hereinafter) of a single species of polyolefin having a number of carbon atoms (hereinafter abbreviated as C) of 2 to 30 or a mixture of two or more thereof [the polymerization method] and a low molecular weight polyolefin obtainable by the thermal degradation method of a high molecular weight polyolefin (a polyolefin obtainable by polymerization of a C2-30 olefin) [the thermal degradation method] can be used as the (a0).

Examples of the C2-30 olefin include ethylene, propylene, C4-30 (preferably 4-12, more preferably 4-10) α-olefin, and a C4-30 (preferably 4-18, more preferably 4-8) diene. Examples of the α-olefin include 1-butene, 4-methyl-1-pentene, 1-pentene, 1-octene, 1-decene and 1-dodecene, and examples of the diene include butadiene, isoprene, 1,4-pentadiene, 1,6-hexadiene, cyclopentadiene and 1,11-dodecadiene. Preferred among these are C2-12 (ethylene, propylene, C4-12 α-olefin, butadiene and/or isoprene, etc.), more preferred are C2-10 (ethylene, propylene, C4-10 α-olefin and/or butadiene, etc.), and particularly preferred are ethylene, propylene and/or butadiene.

The low molecular weight polyolefin obtainable by the thermal degradation method can easily be obtained by the method disclosed in JP-A-3-62804. The polyolefin obtainable by the polymerization method can be produced by a known method, and it can easily be obtained, for example, by a method of (co)polymerizing the olefin in the presence of a radical catalyst, a metal oxide catalyst, a Ziegler catalyst, a Ziegler-Natta catalyst. Of the polyolefins obtainable by the polymerization method or the thermal degradation method, one obtainable by the thermal degradation method is preferred in terms of ease to introduce a carbonyl group which is a modification group, and availability.

The number average molecular weight (hereinafter abbreviated as Mn) of the (a0) determined by gel permeation chromatography (GPC) is preferably 800 to 20,000, more preferably 1,000 to 10,000, and particularly preferably 1,200 to 6,000.

The quantity of double bonds in the (a0) is preferably, from the viewpoint of compatibility, 1 to 40 bonds, more preferably 2 to 30 bonds, and particularly preferably 4 to 20 bonds, per 1000 C.

The average number of double bonds per molecule is preferably, from the viewpoint of ability to form a repetitive structure and the viewpoint of compatibility, 1.1 to 5, more preferably 1.3 to 3, particularly preferably 1.5 to 2.5, and most preferably 1.8 to 2.2.

In the thermal degradation method, a low molecular weight polyolefin the Mn of which is within the range of 800 to 6,000 and the average number of terminal double bonds per molecule of which is 1.5 to 2 can easily be obtained [see, for example, Katsuhide Murata, Tadahiko Makino, The Journal of the Chemical Society of Japan, page 192 (1975)].

Examples of the polyolefin having carbonyl groups on both ends of the polymer (a1) include a polyolefin having a structure formed by modifying both ends of the (a0) with an α,β-unsaturated carboxylic acid (anhydride) (meaning an α,β-unsaturated carboxylic acid, a C1-4 alkyl ester thereof or an anhydride thereof; the same applies hereinafter) (a11), a polyolefin having a structure formed by secondarily modifying the (a11) with a lactam or an aminocarboxylic acid (a12), a polyolefin having a structure formed by oxidizing or hydroformylating the (a0) (a13), a polyolefin having a structure formed by secondarily modifying the (a13) with a lactam or an aminocarboxylic acid (a14), and a mixture of two or more of these.

The Mn of the polyolefin having carbonyl groups on both ends of the polymer (a1) is preferably, from the viewpoints of heat resistance and reactivity with the hydrophilic polymer (b) described later, 800 to 25,000, more preferably 1,000 to 20,000, and particularly preferably 2,500 to 10,000.

The acid value of the (a1) is preferably, from the viewpoint of reactivity with the (b), 4 to 280 (mgKOH/g; hereinafter only a value is specified), more preferably 4 to 100, and particularly preferably 5 to 50.

The (a11) can be obtained by modifying the (a0) with an α,β-unsaturated carboxylic acid (anhydride). Preferred as the α,β-unsaturated carboxylic acid (anhydride) from the viewpoint of reactivity with the (a0) are dicarboxylic acids, alkyl esters thereof, and anhydrides thereof, more preferred are maleic acid (anhydride) and fumaric acid, and particularly preferred is maleic acid (anhydride).

The (a12) can be obtained by secondarily modifying the (a11) with a lactam or an aminocarboxylic acid. Preferred as the lactam and the aminocarboxylic acid from the viewpoint of secondary modification reactivity are caprolactam, laurolactam, glycine, leucine, ω-aminocaprylic acid, 11-aminoundecanoic acid, and 12-aminododecanoic acid, more preferred are caprolactam, laurolactam, ω-aminocaprylic acid, 11-aminoundecanoic acid, and 12-aminododecanoic acid, and particularly preferred are caprolactam and 12-aminododecanoic acid.

The (a13) can be obtained by oxidizing the (a0) by oxygen and/or ozone or hydroformylating the (a0) by the oxo process to introduce a carbonyl group. These methods are known in the art and can be applied appropriately.

The (a14) can be obtained by secondarily modifying the (a13) with a lactam or an aminocarboxylic acid. Examples of the lactam and the aminocarboxylic acid may be those of the listed above with respect to the (a12).

The above-mentioned polymer in the thermoplastic resin (B) is not particularly limited as long as it is one having a hydrophobic block comprising a polyolefin. For example, it may be one having a hydrophilic block, one having a polymer chain other than polyolefin, or the like.

The linkage mode of the hydrophilic block or the polymer chain other than polyolefin with the hydrophobic block comprising a polyolefin may be any of block, random, graft, or a combination thereof.

Of these, an alternating block copolymer (G) in which the hydrophobic block of the polyolefin (a) and the block of the hydrophilic polymer (b) described in detail below are linked via at least one selected from the group consisting of ester linkage, amide linkage, ether linkage and imide linkage can preferably be mentioned.

As the hydrophilic polymer (b), a polyether diol (b1) and a polyether diamine (b2) can be used, for example.

Examples of the polyether diol (b1) include one having a structure obtainable by making an alkylene oxide (hereinafter abbreviated as AO) (C2-12) undergo addition reaction to a diol (b01) or a dihydric phenol (b02), e.g., one represented by formula: $H(OA^1)mO-E^1-O(A^1O)m'H$. In the formula, $E^1$ represents a residue formed by removing a hydroxyl group from the (b01) or the (b02), $A^1$ represents a C2-12 (preferably 2-8, more preferably 2-4) alkylene group optionally comprising a halogen atom; m and m' each represent an integer of 1 to 300, preferably 2 to 250, more preferably 5 to 200, particularly preferably 8 to 150, and most preferably 10 to 100, and m and m' may be the same or different. M $(OA^1)$ residues and m' $(A^1O)$ residues may be the same or different from each other respectively, and the linkage mode in the case that these are constituted of two or more oxyalkylene groups may be any of block, random or a combination thereof.

Examples of the diol (b01) include a C2-12 (preferably 2-10, more preferably 2-8) dihydric alcohol (aliphatic, alicyclic, and araliphatic dihydric alcohols) and a C1-12 tertiary amino group-containing diol. Examples of the aliphatic dihydric alcohol include ethylene glycol, propylene glycol, 1,4-butanediol, 1,6-hexanediol, neopentyl glycol, and 1,12-dodecanediol. Examples of the alicyclic dihydric alcohol include 1,4-cyclohexanediol, 1,4-cyclohexanedimethanol, 1,4-cyclooctanediol, and 1,3-cyclopentanediol. Examples of the araliphatic dihydric alcohol include xylylenediol, 1-phenyl-1,2-ethanediol, and 1,4-bis(hydroxyethyl)benzene.

Examples of the tertiary amino group-containing diol include a bishydroxyalkylated (the alkyl group being C1-12, preferably 2-10, more preferably 2-8) product of an aliphatic or alicyclic primary monoamine (C1-12, preferably 2-10, more preferably 2-8), and a bishydroxyalkylated (the alkyl group being C1-12) product of an aromatic (or araliphatic) primary monoamine (C6-12).

Examples of the aliphatic primary monoamine include methylamine, ethyl amine, 1- and 2-propylamines, n- and i-amylamines, hexylamine, 1,3-dimethylbutylamine, 3,3-dimethylbutylamine, 2- and 3-aminoheptanes, heptylamine, nonylamine, decylamine, undecylamine, and dodecylamine. Examples of the alicyclic primary monoamine include cyclopropylamine, cyclopentylamine, and cyclohexylamine. Examples of the aromatic (or araliphatic) primary monoamine include aniline and benzylamine.

Examples of the dihydric phenol (b02) include C6-18 (preferably 8-18, more preferably 10-15), e.g., monocyclic dihydric phenols (hydroquinone, catechol, resorcin, urushiol, etc.), bisphenols (bisphenol A, bisphenol F, bisphenol S, 4,4'-dihydroxydiphenyl-2,2-butane, dihydroxybiphenyl, etc.), and condensed polycyclic dihydric phenols (dihydroxynaphthalene, binaphthol, etc.).

Preferred among the (b01) and the (b02) are dihydric alcohols and dihydric phenols, more preferred are aliphatic dihydric alcohols and bisphenols, and particularly preferred are ethylene glycol and bisphenol A.

Examples of the AO to be made to undergo addition reaction to the diol (b01) or the dihydric phenol (b02) include C2-12 AOs (ethylene oxide (hereinafter EO), propylene oxide (hereinafter PO), 1,2-, 1,4-, 2,3-, and 1,3-butylene oxides, and mixtures of two or more thereof), and other AOs and substituted AOs may be used together if necessary.

The number of moles of the added AO is preferably, from the viewpoint of the volume resistivity of the hydrophilic polymer (b), 1 to 300 mol, more preferably 2 to 250 mol, and particularly preferably 10 to 100 mol, per one hydroxyl group of the (b01) or the (b02).

The content of the oxyalkylene units in the polyether diol (b1) based on the weight of the (b1) is preferably, from the viewpoint of the volume resistivity of the hydrophilic polymer (b), 5 to 99.8% by weight, more preferably 8 to 99.6% by weight, and particularly preferably 10 to 98% by weight. The content of oxyethylene units in a polyoxyalkylene chain based on the weight of the polyoxyalkylene chain is preferably, from the viewpoint of the volume resistivity of the (b), 5 to 100% by weight, more preferably 10 to 100% by weight, particularly preferably 50 to 100% by weight, and most preferably 60 to 100% by weight.

Examples of the polyether diamine (b2) include one having a structure formed by modifying hydroxyl groups of the polyether diol (b1) with amino groups (primary or secondary amino groups), e.g., one represented by formula:

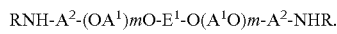
RNH-A²-(OA¹)$m$O-E¹-O(A¹O)$m$-A²-NHR.

Symbol $E^1$ in the formula represents a residue formed by removing a hydroxyl group from the (b01) or the (b02), $A^1$ represents a C2-12 (preferably 2-8, more preferably 2-4) alkylene group optionally comprising a halogen atom; m and m' each represent an integer of 1 to 300, preferably 2 to 250, more preferably 5 to 200, particularly preferably 8 to 150, and most preferably 10 to 100, and m and m' may be the same or different. $A^2$ represents a C2-12 (preferably 2-8, more preferably 2-4) alkylene group optionally comprising a halogen atom, and $A^1$ and $A^2$ may be the same of different. R represents H or a C1-4 (preferably 1 or 2) alkyl group.

The volume resistivity (a value measured with the method described below under a 23° C. and 50% RH atmosphere) of the hydrophilic polymer (b) is preferably $1 \times 10^5$ to $1 \times 10^{11}$ Ω·cm, more preferably $10^6$ to $10^{10}$ Ω·cm, and even more preferably $10^7$ to $10^9$ Ω·cm. One the volume resistivity of which is less than $10^5$ have deteriorated resin physical properties, and if exceeding $10^{11}$, the compatibility is deteriorated.

The Mn of the (b) is preferably, from the viewpoints of heat resistance and reactivity with the polyolefin (a), 150 to 20,000, more preferably 300 to 18,000, even more preferably 1,000 to 15,000, and most preferably 1,200 to 8,000.

In the present invention, the alternating block copolymer (G) refers to any substances having a structure in which a block of the above-described polyolefin (a) and a block of the hydrophilic polymer (b) are linked repeatedly and alternately via at least one selected from the group consisting of ester linkage, amide linkage, ether linkage and imide linkage. Preferable among them may, for example, be a polymer having a repeating unit represented by the following formula (1):

[Chemical Formula 1]

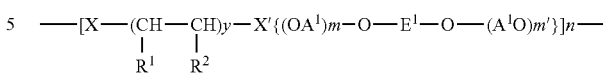

In the above formula, n is an integer of 2 to 50 (preferably 3 to 40, more preferably 4 to 30); and $R^1$ and $R^2$ are each independently a hydrogen atom or a methyl group, provided that not both of $R^1$ and $R^2$ are methyl groups. y is an integer of 15 to 800 (preferably 20 to 500, more preferably 30 to 400). $E^1$ is an alkylene group having 1 to 11 carbon atoms or a phenylene group (a residue formed by removing a hydroxyl group from the diol (b01) or the dihydric phenol (b02)). $A^1$ is an alkylene group having 2 to 12 (preferably 2 to 8, more preferably 2 to 4) carbon atoms and having optionally a halogen atom. m and m' are each independently an integer of 1 to 300 (preferably 2 to 250, more preferably 5 to 200, particularly preferably 8 to 150, most preferably 10 to 100).

X is a group represented by the formula (2) or the formula (3), and X' is a group represented by the formula (2') or the formula (3'). It is noted that X' is a group represented by the formula (2') when X is a group represented by the formula (2), and X' is a group represented by the formula (3') when X is a group represented by the formula (3).

[Chemical Formula 2]

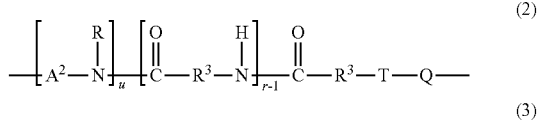

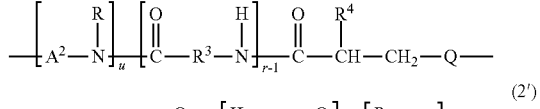

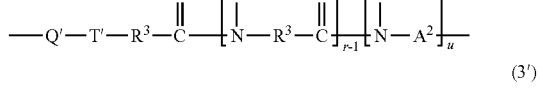

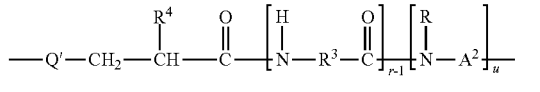

In the formulae (2), (3), (2') and (3'), R is a hydrogen atom or an alkyl group having 1 to 4 (preferably 1 or 2) carbon atoms. $R^3$ is an alkylene group having 1 to 11 (preferably 2 to 11, more preferably 5 to 11) carbon atoms. $R^4$ is a hydrogen atom or an alkyl group having 1 to 10 (preferably 1 to 8, more preferably 1 to 6) carbon atoms. $A^2$ is an alkylene group having 2 to 12 carbon atoms and having optionally a halogen atom. r is an integer of 1 to 20 (preferably 1 to 15, more preferably 1 to 10), and u is 0 or 1.

Q is a group represented by the formula (4). Q' is a group represented by the formula (4'). T is a group represented by the formula (5). T' is a group represented by the formula (5').

[Chemical Formula 3]

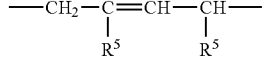

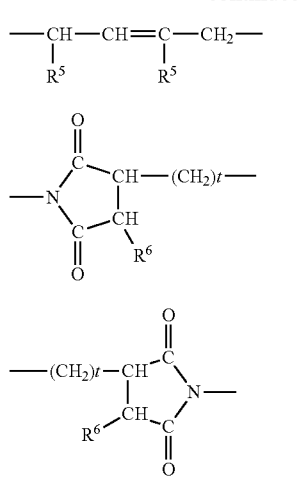

In the formulae (4), (4'), (5) and (5'), $R^5$ is a hydrogen atom or an alkyl group having 1 to 10 (preferably 1 to 8, more preferably 1 to 6) carbon atoms. $R^6$ is a hydrogen atom or a methyl group. t is 1 when $R^6$ is a methyl group, and t is 0 when $R^6$ is a hydrogen atom.

The polyether segment within { } in the repeating unit represented by the formula (1), namely {$(OA^1)mO-E^1-O(A^1O)m$} is a structure derived from the above-mentioned polyether diol (b1) or polyether diamine (b2), and $E^1$, $A^1$, m, and m' in the formula are as previously described.

A block polymer in which X is a group represented by the formula (2) and X' is a group represented by the formula (2') in the formula (1) includes (A-1) obtainable by making (a11) and/or (a12) undergo a polymerization reaction with (b1), and (A-2) obtainable by making (a11) and/or (a12) undergo a polymerization reaction with (b2). The (A-1) includes (A-11) in which (a11) and (b1) are combined, (A-12) in which (a12) and (b1) are combined, and a mixture of the (A-11) and the (A-12). Likewise, the (A-2) includes (A-21) in which (a11) and (b2) are combined, (A-22) in which (a12) and (b2) are combined, and a mixture of the (A-21) and the (A-22).

The (A-1) can be produced by methods known in the art, for example, a method in which (b1) is added to (a11) and/or (a12) and a polymerization (polycondensation) reaction is performed under reduced pressure, usually at 200 to 250° C. or a method in which polymerization is performed usually at 160 to 250° C. for a residence time 0.1 to 20 minutes by using a single screw or twin screw extruder. The method disclosed in JP-A-2007-146145 can be referred to.

Of the (A-1), the (A-12) may be produced by secondarily modifying (a11) with a lactam or an aminocarboxylic acid, which are previously mentioned, and then adding (b1) and reacting them, or by reacting (a11) and a lactam or an aminocarboxylic acid in the presence of (b1), and subsequently reacting them with (b1).

The (A-2) can be produced by the same method as that for the (A-1) except that the combination of (a11) and/or (a12) and the (b1) in the (A-1) is changed to a combination of (a11) and/or (a12) and (b2). Of the (A-2), the (A-22) may be produced by secondarily modifying (b2) with a lactam or an aminocarboxylic acid, which are previously mentioned, and then reacting the resultant with (a11).

A block polymer in which X is a group represented by the formula (3) and X' is a group represented by the formula (3') in the formula (1) includes (A-3) obtainable by making (a13) (when r=1) and/or (a14) (when R≥2) and (b1) undergo a polymerization reaction, and (A-4) obtainable by making (a13) and/or (a14) and (b2) undergo a polymerization reaction. The (A-3) includes (A-31) in which (a13) and (b1) are combined, (A-32) in which (a14) and (b1) are combined, and a mixture of the (A-31) and the (A-32). Likewise, the (A-4) includes (A-41) in which (a13) and (b2) are combined, (A-42) in which (a14) and (b2) are combined, and a mixture of the (A-41) and the (A-42). The (A-3) and the (A-4) can be produced by methods similar to those for the (A-1) and the (A-2).

The quantity of the (b) constituting the alternating block copolymer (G) is preferably, from the viewpoint of compatibility, 20 to 90% by weight, more preferably 25 to 80% by weight, particularly preferably 30 to 70% by weight, based on the total weight of the (a) and the (b).

The Mn of the alternating block copolymer (G) is preferably 2,000 to 60,000, more preferably 5,000 to 40,000, and particularly preferably 8,000 to 30,000. If the Mn is within this range, the (G) does not bleed out with time. The Mn can be measured by the GPC method in a procedure known in the art.

In the structure of the alternating block copolymer (G), the average number of repetitions (Nn) of the repeating unit of the block of the polyolefin (a) and the block of the hydrophilic polymer (b) is preferably 2 to 50, more preferably 3 to 40, and even more preferably 4 to 30. As to the Nn, the ratio of the integrals of the protons is calculated by a known method by $^1$H-NMR, for example, signals assigned to some desired protons are measured, and then the Nn can be calculated from the ratio and the Mn of the (G).

Each end of the alternating block copolymer (G) is a carbonyl group, an amino group and/or a non-modified polyolefin end (a polyolefin end not having been subjected to any modification, namely, an alkyl group or an alkenyl group) derived from (a), or a hydroxyl group and/or an amino group derived from (b). Of these, preferred as an end from the viewpoint of reactivity are a carbonyl group, an amino group and a hydroxyl group, and more preferred are a carbonyl group and a hydroxyl group.

In the core-shell type water-absorbing resin particle of the present invention, the (B) described above may be a thermoplastic resin having a sea-island structure composed of islands formed by more polar domains and the sea formed by less polar domains.

When the thermoplastic resin (B) is a thermoplastic resin having the above-described sea-island structure, the thermoplastic resin (B) may preferably be a resin obtained by polymerizing at least one radically polymerizable monomer (E) selected from the group consisting of styrenic compounds, vinyl group-containing carboxylic acids or the derivatives thereof, and (meth)acrylonitrile in a heat-melt kneader in the presence of an α-olefin (co)polymer (C) composed of an α-olefin homopolymer (C1) and/or an ethylene/α-olefin copolymer (C2) and a low viscosity polyolefin resin (D). The (C) or (D) can have the structure of a hydrophobic block comprising a polyolefin, which the thus-obtained thermoplastic resin has.

Specific examples of the α-olefin homopolymer (C1) include homopolymers of propylene, 1-butene, 1-pentene, 4-methyl-1-pentene, etc. Specific examples of the ethylene/α-olefin copolymer (C2) include copolymers of ethylene with the above-described α-olefins. Examples of the (C1) and the (C2) include graft modified bodies of these (co) polymers with vinyl group-containing carboxylic acids [e.g., (meth)acrylic acid, maleic acid (anhydride), fumaric acid, and itaconic acid], and blends of two or more of these (co)polymers or modified bodies.

Specific examples of the α-olefin (co)polymer (C) include the (C1), the (C2), and graft modified bodies of these (co)polymers with vinyl group-containing carboxylic acids [e.g., (meth)acrylic acid, maleic acid (anhydride), fumaric acid, and itaconic acid], and blends of two or more of these (co)polymers or modified bodies. Preferred among these are a butene-1 homopolymer and an ethylene/butene-1 copolymer.

The melt index of the (C1) measured by the ASTM D1238-L method (230° C., 2160 g) is preferably 1 to 100, more preferably 5 to 50. If the melt index of the (C1) exceeds 100, the oil resistance may be insufficient, and if the melt index is less than 1, sufficient processability may not be acquired.

The melt index of the (C2) measured by the ASTM D1238-L method (230° C., 2160 g) is preferably 10 to 100, more preferably 10 to 50. If the melt index of the (C2) exceeds 100, the oil resistance may be insufficient, and if the melt index is less than 10, sufficient processability may not be acquired.

Examples of the low viscosity polyolefin resin (D) include a low molecular weight polyolefin copolymer obtainable by thermal degradation or a polypropylene (co)polymer having a degree of crystallization of 10% or less obtained by a publicly known polymerization method, and their graft modified bodies with vinyl group-containing carboxylic acids [e.g., (meth)acrylic acid, maleic acid (anhydride), fumaric acid, and itaconic acid]. The propylene unit content in the (D) is preferably 30% by weight or more, more preferably 50% by weight or more. If the propylene content in the (D) is less than 30% by weight, the heat resistance of the thermoplastic resin (B) may deteriorate.

The melt viscosity of the (D) at 190° C. is preferred 30 to 100,000 cP, more preferably 40 to 20,000 cP. If the melt viscosity is less than 30 cP, the strength of the thermoplastic resin (B2) may be insufficient, and if the melt viscosity exceeds 100,000 cP, the thermoplastic resin (B2) becomes higher in viscosity and therefore the processability and the applicability may deteriorate.

The radically polymerizable monomer (E) may be at least selected from the group consisting of styrenic compounds, vinyl group-containing carboxylic acids or derivatives thereof, and (meth)acrylonitrile. Preferred among these in terms of thermal stability are styrenic compounds and combinations of styrenic compounds with other monomers mentioned above.

Examples of said styrenic compounds include styrene, t-butylstyrene, α-methylstyrene, p-methylstyrene, chlorostyrene, bromostyrene, fluorostyrene, ethylstyrene, divinylbenzene, and N,N-diethylaminostyrene. Particularly preferred among these is styrene.

Examples of said vinyl group-containing carboxylic acids or derivatives thereof include vinyl group-containing carboxylic acids [e.g., (meth)acrylic acid, maleic anhydride, fumaric acid, and itaconic acid], (meth)acrylates [e.g., alkyl having 1 to 18 carbon atoms (methyl, ethyl, propyl, octyl, dodecyl, etc.) (meth)acrylates, alicyclic alkyl having 6 to 12 carbon atoms (cyclohexyl, dicyclohexyl, etc.) (meth)acrylates, aralkyl having 7 to 21 carbon atoms (benzyl, etc.) (meth)acrylates, hydroxyalkyl (having 2 to 6 carbon atoms) (meth)acrylates, and glycidyl (meth)acrylate], and imidates of vinyl group-containing dicarboxylic acids [maleimide, N-methylmaleimide, N-butylmaleimid, N-phenylmaleimide, etc.]. Preferred among these are (meth)acrylic acid, maleic anhydride, and esterified products thereof.

In the thermoplastic resin (B) having the above-described sea-island structure, the weight ratio of (C), (D) and (E), namely (C):(D):(E), is preferably 100:(30 to 300):(1 to 50), more preferably 100:(50 to 200):(3 to 30). If the proportion of the (D) is less than 30, the resulting thermoplastic resin (B) may be high in viscosity, and if the proportion exceeds 300, the rubber elasticity of the thermoplastic resin (B) drops. In addition, if the proportion of the (E) is less than 1, the cohesive force is weak and the strength of the thermoplastic resin (B) is insufficient, and if the proportion exceeds 50, the melt viscosity of the thermoplastic resin (B) becomes high and therefore the processability becomes insufficient.

In order to further enhance the reduction in viscosity of the thermoplastic resin (B) having the above-described sea-island structure, (liquefied) hydrogenated polybutadiene (J) may be incorporated, if necessary. If the (J) is used, the content thereof is preferably 50% by weight or less, more preferably 30% by weight or less. If the proportion of the (J) exceeds 50% by weight, the cohesive force of the thermoplastic resin (B) drops.

The thermoplastic resin (B) having a sea-island structure has a sea-island structure composed of an island formed of a domain having a higher polarity and a sea formed of a domain having a lower polarity. The method for producing such a thermoplastic resin (B) is not particularly limited, and examples thereof include the methods enumerated below:

(1) a method of mixing a material prepared by polymerizing (E) in the presence of (C) beforehand and a material prepared by polymerizing (E) in the presence of (D);
(2) a method of polymerizing (E) in the presence of both of (C) and a material prepared by polymerizing (E) in the presence of (D);
(3) a method of polymerizing (E) in the presence of both of (D) and a material prepared by polymerizing (E) in the presence of (C); and
(4) a method of polymerizing (E) in the presence of (C) and (D).

Of these, preferred is the method (4).

The thermoplastic resin (B) having a sea-island structure can be obtained, for example, by polymerizing the feedstock to be used in these methods, in a heat-melt kneader. The heat-melt kneader to be used for the above polymerization is not particularly limited in terms of its style, shape, and the like, and examples thereof include a mixer having a compressively shaped screw having a reverse screw part or a ribbon stirrer, a kneader, an extruder, and a mixer. Of these, use of a non-open apparatus is preferred, and it is preferred to perform kneading in an inert gas atmosphere such as nitrogen during the polymerization.

In this case, preferably, the thermoplastic resin (B) having a sea-island structure may be obtained by using a continuous mixer, feeding a mixture of dispersed raw materials from a raw material feeding port of the continuous mixer, then performing polymerization while keeping a residence time, and removing monomers from the resulting mixture with a twin screw extruder or the like.

In the polymerization, polymerization initiators and organic solvents known in the art can be used if necessary. Examples of the polymerization initiators include organic peroxides such as ketone peroxides, peroxyketals, hydroperoxides, dialkyl peroxides, diacyl peroxides, peroxydicarbonates, and peroxyesters, and azo compounds such as azoisobutyronitrile. Examples of the organic solvents include alicyclic hydrocarbon solvents, aromatic hydrocarbon solvents, alcohol solvents, halogen-based solvents, ketone solvents, and ether solvents.

Although the temperature of the polymerization is not particularly limited and may be any temperature at which monomers are substantially allowed to polymerize, it is usually 80 to 260° C.

The thermoplastic resin having a melting point of 50 to 180° C. (B) contained in the layer of the shell layer (Q) layer described above may optionally further comprise a low molecular weight polyolefin (H) and/or a plasticizer (I).

Examples of the low molecular weight polyolefin (H) include polypropylene, polyethylene, copolymers of propylene with one or more other vinyl compounds [ethylene, α-olefins (C4-12, e.g., 1-butene and 4-methyl-1-pentene), vinyl acetate, (meth)acrylic acid, etc.], graft modified bodies of these (co)polymers modified with unsaturated carboxylic acids (anhydrides) [those enumerated above, e.g., maleic acid (anhydride)], and blends of two or more of these copolymers or modified bodies. Of these, polypropylene, polyethylene, propylene/ethylene copolymers, and their graft modified bodies modified with unsaturated carboxylic acids (anhydrides) are preferred from the viewpoint of compatibility, and more preferred are polypropylene and graft modified bodies of polypropylene modified with unsaturated carboxylic acids (anhydrides).

The Mn of the low molecular weight polyolefin (H) is preferably 500 or more, more preferably 800 or more, particularly preferably 1,000 or more, and preferably 25,000 or less, more preferably 23,000 or less, and particularly preferably 20,000 or less.

The amount of the (H) used is preferably 30% by weight or less, more preferably 0.1 to 25% by weight, and even more preferably 0.5 to 20% by weight, based on the weight of the (B).

As the plasticizer (I), known plasticizers, for example, liquid resins [weight average molecular weight (hereinafter abbreviated as Mw; measured by GPC)=300 to 10,000], such as paraffinic, naphthenic, or aromatic process oils, liquid polybutene, liquid polybutadiene, and liquid polyisoprene, hydrogenated bodies of these liquid resins, natural or synthetic waxes {paraffin wax, microcrystalline wax, and low molecular weight polyolefin wax (Mw=1,000 to 30,000), etc.}, and mixtures of two or more of these are used. Of these, paraffinic process oil, naphthenic process oil, and mixtures thereof are preferred from the viewpoints of thermal stability and weatherability.

The amount of the (I) used is preferably 50% by weight or less, more preferably 1 to 45% by weight, and even more preferably 5 to 40% by weight, based on the total weight of the (B).

In the core-shell type water-absorbing resin particle of the present invention, the weight ratio of the thermoplastic resin (B) to the water-absorbing resin (A) is preferably 0.1 to 10% by weight. If the ratio exceeds this range, the absorption performance and the absorption rate which the (A) originally has and the softness of a resulting absorber deteriorate. On the other hand, when the ratio is lower than that range, the fixation of the (A) to the fibrous base material (F) deteriorates and the shape retention after water absorption of a resulting absorber is inferior.

For the core-shell type water-absorbing resin particle of the present invention, other additives for resin may be used if necessary, and examples thereof include at least one selected from the group consisting of a colorant, a filler, a nucleating agent, a lubricant, a release agent, an antioxidants, a flame retardant, a UV absorber, and an antibacterial agent. As these additives, one known in the art can be used in procedures such as a known loading.

As to the method for producing the core-shell type water-absorbing resin particle of the present invention, a resin particle produced by any method through any course is available, and examples of the method for producing a core-shell type resin particle include the production methods (I) to (III) as described below:

(I): A method in which a core particle is produced and, at the same time, a core-shell structure is formed.

A method in which an aqueous dispersion liquid (W) of resin particles made of a thermoplastic resin (B) is mixed with a water-absorbing resin (A) or a solvent solution thereof to disperse the water-absorbing resin (A) or the solvent solution thereof in the (W) and resin particles made of the water-absorbing resin (A) are formed in the (W).

In this case, resin particles made of the water-absorbing resin (A) are formed and, at the same time, resin particles made of the thermoplastic resin (B) adhere to the surface of the aforesaid resin particles, so that an aqueous dispersion liquid of core-shell type resin particles constituted of a core layer (P) and a shell layer (Q) is formed, and the aqueous medium is then removed therefrom.

(II): A method in which resin particles produced beforehand from a water-absorbing resin (A) are coated with a coating agent (W') made of a thermoplastic resin (B), and then core-shell type resin particles are produced by further forming a shell layer into a film form, if necessary.

In this case, the method of the coating is not limited, and examples thereof include a method of dispersing resin particles produced beforehand from a water-absorbing resin (A) in an aqueous dispersion liquid (W') made of a thermoplastic resin (B), and a method in which a solution of a thermoplastic resin (B) is sprinkled as a coating agent over resin particles produced beforehand from a water-absorbing resin (A).

(III): A method in which resin particles produced beforehand from a water-absorbing resin (A) are mixed with a thermoplastic resin (B) synthesized beforehand in a mixer, and then subjected to heat treatment, thereby obtaining water-absorbing resin particles in which the surface of resin particles of the water-absorbing resin (A) is coated with the thermoplastic resin (B).

Of these, the production method (III) is preferred.

The core-shell type water-absorbing resin particle may be in any shape, such as a grained shape, a granular shape, a granulated shape, a scaly shape, a massive shape, a pearl shape, and a particulate shape. It is preferred that 90% by weight or more of the particle be in a powdery shape having a particle size distribution of 1 mm or less, and it is particularly preferred that 90% by weight or more of the particle be a grained, granular, granulated, scaly or massive water-absorbing resin particle having a particle size distribution of 0.1 to 0.9 mm.

In the absorber of the present invention, a water-absorbing resin particle of the present invention is fixed to a fibrous base material (F).

The fibrous base material (F) is preferably one or more selected from the group consisting of a cellulosic fiber, an organic synthetic fiber, and a mixture of a cellulosic fiber and an organic synthetic fiber. Examples of the cellulosic fiber include natural fibers such as fluff pulp and cellulosic chemical fibers such as viscose rayon, acetate rayon, and cuprammonium rayon. Such cellulosic natural fibers are not particularly limited with respect to their raw material (needle-leaf trees, broadleaf trees, etc.), production method ((chemical pulp, semichemical pulp, mechanical pulp, CTMP, etc.), bleaching method, etc. Examples of the organic synthetic fiber include polypropylene fiber, polyethylene fiber, polyamide fiber, polyacrylonitrile fiber, polyester fiber, polyvinyl alcohol fiber, polyurethane fiber, and heat-weldable composite fiber (e.g., fiber in which at least two of said fibers differing in melting point are hybridized in a sheath-core type, an eccentric type, a parallel type, fiber in which at least two of said fibers are blended, and fiber in which the surface layer of said fibers is modified, etc.). Preferred among these fibrous base materials are cellulosic natural fiber, polypropylene fiber, polyethylene fiber, polyester fiber, heat-weldable composite fiber, and mixed fiber thereof, and fluff pulp, heat-weldable composite fiber, and mixtures thereof are more preferred in that a resulting absorber is excellent in shape retention after water absorption.

The fibrous base material (F) is not particularly limited in length and thickness, and usually, it can suitably be used if its length is within a range of 1 to 200 mm and its thickness is within a range of 0.1 to 100 deniers. The shape thereof is not particularly limited if it is fibrous, and examples of the shape include narrow cylindrical form, split yarn form, staple form, filament form and web form.

As to the ratio of the water-absorbing resin particle and the fibrous base material (F), the weight ratio of the water-absorbing resin particle:the fibrous base material (F) is from (20:80) to (95:5), more preferably from (30:70) to (90:10), even more preferably from (35:65) to (80:20). When the ratio of the water-absorbing resin particle is less than 20, the performance of a resulting absorber cannot be fully developed, and when the ratio exceeds 95, the shape retention of a water absorber after absorption is inferior.

As a method of fixing water-absorbing resin particles to a fibrous base material (F), an appropriate known method can be employed according to the properties of the (F). In this case, a heat-weldable composite fiber of at least one selected from among sheath-core type, eccentric type and parallel type, comprising a plurality of (two or more) components differing in melting point wherein the melting point of a low melting point component is 50 to 180° C. is preferred as the above-mentioned organic synthetic fiber because it allows employment of a simple method of heating in order to attain fixation.

Examples of the method for producing a water absorber of the present invention include (1) a method in which water-absorbing resin particles are mixed with a fibrous base material (F) or sprinkled to the (F), and subsequently are treated at a temperature equal to or higher than the melting point of the thermoplastic resin (B) contained in the shell layer of the water-absorbing resin particles, (2) a method in which water-absorbing resin particles are mixed with a fibrous base material (F) at a temperature equal to or higher than the melting point of the (B) and the water-absorbing resin particles are partially fixed to the fibrous base material (F) during the mixing, (3) a method in which water-absorbing resin particles are kept at a temperature equal to or higher than the melting point of the (B) beforehand and are sprinkled, applied or adhered to a fibrous base material (F), and (4) a method in which water-absorbing resin particles are sprinkled to or mixed with a fibrous base material (F) kept at a temperature equal to or higher than the melting point of the (B).

The device for mixing the water-absorbing resin particles with the fibrous base material (F) may be a usual mixing device, and examples thereof include a conical blender, a Nauter mixer, a V type mixer, a fluidized bed type mixer, an air flow type mixing device, an air flow type mixing device equipped with a nozzle for spraying particles, and a crushing device for fibrous materials equipped with a nozzle for spraying particles. Examples of the device for treating at a temperature equal to or higher than the melting point of the (B) include a hot air heater, a Nauter type heater, a fluidized bed type heater, an air flow type heater, a heating type calender roll, an infrared heater, and a high frequency heater.

In the present invention, not all the water-absorbing resin particles is necessarily required to be fixed to the fibrous base material (F), and apart, for example, 50% by weight or more, of the water-absorbing resin particles should just be fixed. Choice of proper conditions will lead to 60% by weight or more. When the fixation ratio is less than 50% by weight, application to an absorbent article such as disposable diapers or sanitary products may result in movement, maldistribution, separation, or shedding of water-absorbing resin particles during a course of storage or transportation of those products.

In the absorber of the present invention, the above-mentioned fixation ratio is preferably a value after a vibration test. The vibration test can be performed using a Ro-Tap test sieve shaker and standard sieves (JIS Z8801-1:2006), for example.

The absorber of the present invention may be subjected to treatment which is usually applied to fibrous materials, such as crushing, lamination, compression, cold calendering, heat calendering, needle punching, stretching, and sheet making.

Organic powders (e.g., pulp powder, cellulose derivatives, and natural polysaccharides), inorganic powders (e.g., zeolite, silica, alumina, bentonite, and activated carbon), glass fibers, antioxidants, antiseptic agents, bactericides, surfactants, colorants, flavors, etc. may be incorporated in the absorber of the present invention as an extender or an additive, if necessary. The quantity thereof is usually 10% by weight or less, preferably 5% by weight or less, relative to the weight of the absorber.

The absorbent article of the present invention is one using the absorber of the present invention. Examples of the absorbent article include various types of hygienic materials and absorbent articles such as disposable diapers, sanitary products, maternity pads, and medical under pads. Especially, it is useful for thin disposable diapers or thin sanitary products which are large in the water-absorbing resin/fiber (pulp and/or heat-weldable fiber) ratio. Moreover, it is useful also when producing sheet-like or tape-like water-absorbing materials, such as freshness preservation materials for fruits and vegetables, drip absorbers, moisture or humidity regulation sheets, materials for the prevention of dew formation, raising seedling sheets for paddy rice, concrete aging sheets, water-blocking materials for telecommunication cables and optical fiber cables. The configuration and the structure of these absorbent articles are well known by persons skilled in the art.

EXAMPLES

The present invention will be described byway of examples and comparative examples, but the present invention is not limited to them.

A fixation ratio, a water absorption rate, and shape retention after water absorption were measured by the methods described below. Hereafter, unless otherwise stated, "part" means "part by weight" and "%" means "% by weight."

Water Absorption Rate: One gram of an absorber was put into a 250 mesh tea bag made of nylon, and this was immersed in large excess of 0.9% aqueous sodium chloride solution for 2 minutes, then hung for 15 minutes to dewater, and then the weight increase was measured. A value obtained by dividing the measured value by 2 minutes was evaluated as an absorption rate.

Fixation Ratio: Using a RO-TAP sieve shaker and standard sieves (JIS Z8801-1:2006), an absorber is put on an 850 μm sieve and it is shaken with the RO-TAP sieve shaker for 5 minutes. From the weight (W) of absorbent resin particles that shed on a saucer, a fixation ratio was calculated.

When the weight of the water-absorbing resin particles contained in the absorber before the test is denoted by W0, the fixation ratio is calculated from the following formula.

Fixation ratio (%)={(W0−W)/W0}×100

Shape Retention: Ten grams of water-absorbing material was allowed to absorb 200 ml of physiological saline and then it was put on a wire net with an opening size of 4 mm. The wire net was vibrated, and the shape retention of the water-absorbing material after the water absorption and the shedding of swollen water-absorbing resin were observed and evaluated on the following criteria.
⊙: Shape retention is good and almost no shedding of water-absorbing resin is observed.
○: Shape retention is good and only a little shedding of water-absorbing resin is observed.
Δ: The shape is retained to some extent, but much shedding of water-absorbing resin is observed.
x: The shape is not retained and much shedding of water-absorbing resin is observed.

Production Example 1

While stirring and mixing 88 parts of sodium acrylate, 22.85 parts of acrylic acid, 0.3 parts of N,N'-methylenebisacrylamide, and 293 of deionized water, the temperature was kept at 1 to 2° C., nitrogen was flowed into this mixture liquid, and the concentration of oxygen dissolved in the mixture liquid was adjusted to 0.5 ppm or less. Subsequently, 0.3 parts of a 1% by weight aqueous hydrogen peroxide solution, 0.8 parts of a 0.2% by weight aqueous ascorbic acid solution, and 0.8 parts of a 2% by weight aqueous 2,2'-azobisamidinopropane dihydrochloride solution were added to that mixture liquid and mixed, thereby starting polymerization, and after the reaction solution reached 80° C., polymerization was performed at a polymerization temperature of 80° C.±2° C. for about 5 hours. Thus, a hydrous resin (gel 1) was obtained.

This hydrous resin (gel 1) in an amount of 400 parts was minced with a mincer (12VR-400K, manufactured by Iizuka Kogyo K.K., hole diameter of catch basin: 6 mm) at 25° C. for 5 minutes and then dried in a ventilated band drier (135° C., 2.0 m/second; Inoue Kinzoku Kogyo Co., Ltd.), thereby obtaining a dried polymer.

This dried polymer was pulverized with a juicing blender (National MX-X53, manufactured by Matsushita Electric Co., Ltd.), and was controlled to within the particle diameter range of 150 to 710 μm using sieves having sieve-openings of 150 and 710 μm. Then, while stirring 100 parts of this at high speed (a high-speed stirring turbulizer manufactured by Hosokawa Micron Corporation; rotation speed: 2000 rpm), 5.5 parts of a 1% by weight water/methanol mixed solution (weight ratio of water/methanol=60/40) of ethylene glycol diglycidyl ether was added by spraying and mixed, and the resultant was allowed to stand at 140° C. for 30 minutes to achieve heat crosslinking (surface crosslinking). Thus, a granular water-absorbing resin (A1) was obtained.

Production Example 2

After mixing 90 parts of a low molecular weight ethylene/propylene random copolymer (Mn: 3,500, density: 0.89, the amount of double bonds per 1,000 carbon atoms: 7.1, the average number of double bonds per molecule: 1.8, the content of polyolefin capable of being modified at both ends: 90%) obtained by thermal degradation [an ethylene/propylene random copolymer (ethylene content: 2%) having a density at 23° C. of 0.90 (unit: g/cm$^3$, hereafter only a value is shown) and an MFR of 6.0 g/10 minutes was thermally degraded at 410±0.1° C.], 10 parts of maleic anhydride, and 30 parts of xylene, they were melted at 200° C. under a nitrogen gas atmosphere (sealed), and were allowed to react at 200° C. for 20 hours. Then, excess of maleic anhydride and xylene were distilled off under reduced pressure, at 200° C. in 3 hours, thereby obtaining an acid-modified polypropylene (a1). The acid value was 27.2 and the Mn was 3,700.

Sixty-six parts of the (a1) and 34 parts of 1,2-aminododecanoic acid were melted at 200° C. in a nitrogen gas atmosphere, and then allowed to react at 200° C. for 3 hours under a reduced pressure of 10 mmHg or less, thereby obtaining an acid-modified polypropylene (a2). The acid value of (a2) was 17.7 and the Mn was 5,700.

To a stainless steel autoclave were added 60 parts of the acid-modified polypropylene (a2), 33 parts of polyethylene glycol (Mn: 3,200, volume resistivity: 3×10$^8$ Ω·cm), 7 parts of sodium dodecylbenzenesulfonate, 0.3 parts of an antioxidant [IRGANOX 1010, produced by Ciba Specialty Chemicals; the same applies hereafter], and 0.5 parts of zinc acetate, which were then allowed to polymerize at 230° C. under a reduced pressure of 1 mmHg or less for 4 hours, thereby obtaining a viscous polymer. This polymer was taken out in a strand shape on a belt and pelletized, thereby obtaining a block polymer (a3). The Mn of (a3) was 28,000 and the melting point was 121° C. The average number of repetitions Nn of (a3) determined from the Mn and $^1$H-NMR analysis was 3.4.

Production Example 3

After mixing 94 parts of a low molecular weight polypropylene (Mn: 10,000, density: 0.89, the amount of double bonds per 1,000 carbon atoms: 1.3, the average number of double bonds per molecule: 1.8, the content of polyolefin capable of being modified at both ends: 90% by weight) obtained by thermal degradation [a polypropylene having a density at 23° C. of 0.90 and an MFR of 10 (g/10 minutes) was thermally degraded at 410±0.1° C.], 6 parts of maleic anhydride, and 30 parts of xylene, an acid-modified polypropylene (a4) was obtained in the same manner as Production Example 1. The acid value of (a4) was 5.0 and the Mn was 10,000.

To a stainless steel autoclave were added 71 parts of the acid-modified polypropylene (a4), 2 parts of 1,2-aminododecanoic acid, 25 parts of α,ω-diaminopolyethylene glycol (Mn: 8,000, volume resistivity: 3×10$^7$ Ω·cm), 0.5 parts of lithium trifluoromethanesulfonate, 0.3 parts of an antioxidant, and 0.5 parts of zirconyl acetate, which were then allowed to polymerize at 230° C. under a reduced pressure of 1 mmHg or less for 5 hours, thereby obtaining a viscous polymer. Then, a block polymer (a5) was obtained in the same manner as Production Example 2. The Mn of (a5) was 36,000. The average number of repetitions Nn of (a5) determined from the Mn and $^1$H-NMR analysis was 2.0, and the melting point was 128° C.

Example 1

Twenty parts by weight of the granular water-absorbing resin (A1) produced in Production Example 1 and 0.2 parts by weight of the block copolymer (a3) synthesized in Production Example 2 were charged into a V-type mixer and mixed for 20 minutes, and then subjected to heat treatment at 150° C. for 15 minutes, thereby obtaining a water-absorbing resin particle (1) whose surface had been coated with a block polymer.

Subsequently, a core-sheath type polyester/polyethylene fiber (the melting point of a lower melting point component was not lower than 50° C. and lower than 150° C.) was fibrillated with a defibrating machine for synthetic fibers (manufactured by Daiwa-Kiko Co., Ltd.) and then subjected to web formation with a sample roller carding machine (ISC-360, manufactured by Intec, INC.). Twenty parts by weight of the water-absorbing resin particles (1) were scattered to 5 parts by weight of the web-like core-sheath type polyester/polyethylene fiber and then subjected to heat treatment at 150° C. for 5 minutes, thereby obtaining an absorber (1).

Example 2

An absorber (2) was obtained in the same manner except that the block polymer (a3) used in Example 1 was replaced by the block polymer (a5) synthesized in Production Example 3.

Comparative Example 1

An absorber (3) was obtained in the same manner except that the block polymer (a3) used in Example 1 was replaced by an acid-modified wax (molecular weight: 1,500, acid value: 60, melting point: 104° C.).

Comparative Example 2

An absorber (4) was obtained in the same manner except that the block polymer (a3) used in Example 1 was replaced by an ethylene vinyl acetate (viscosity: 595 mPa·s, melting point: 92° C.)

Comparative Example 3

An absorber (5) was obtained in the same manner except that the addition amount of the acid-modified wax used in Comparative Example 1 was changed to 1 part by weight.

Comparative Example 4

An absorber (6) was obtained in the same manner except that the amount of the ethylene vinyl acetate used in Comparative Example 2 was changed to 1 part by weight.

The results of water absorption rate, fixation ratio, and shape retention measured for the absorbers (1) to (6) obtained in Examples 1 and 2 and Comparative Examples 1 to 4 are shown in Table 1.

TABLE 1

| | Absorber | Water absorption rate (g/min) | Fixation ratio (%) | Shape retention |
| --- | --- | --- | --- | --- |
| Example 1 | (1) | 18 | 88 | ⊙ |
| Example 2 | (2) | 16 | 91 | ◯ |
| Comparative Example 1 | (3) | 17 | 23 | X |
| Comparative Example 2 | (4) | 17 | 37 | X |

TABLE 1-continued

| | Absorber | Water absorption rate (g/min) | Fixation ratio (%) | Shape retention |
| --- | --- | --- | --- | --- |
| Comparative Example 3 | (5) | 5 | 85 | ◯ |
| Comparative Example 4 | (6) | 6 | 89 | Δ |

Production Example 4

While stirring and mixing 88 parts of sodium acrylate, 22.85 parts of acrylic acid, 0.3 parts of N,N'-methylenebisacrylamide, and 293 of deionized water, the temperature was kept at 1 to 2° C., nitrogen was flowed into this mixture liquid, and the concentration of oxygen dissolved in the mixture liquid was adjusted to 0.5 ppm or less. Subsequently, 0.3 parts of a 1% by weight aqueous hydrogen peroxide solution, 0.8 parts of a 0.2% by weight aqueous ascorbic acid solution, and 0.8 parts of a 2% by weight aqueous 2,2'-azobisamidinopropanedihydrochloride solution were added to that mixture liquid and mixed, thereby starting polymerization, and after the reaction solution reached 80° C., polymerization was performed at a polymerization temperature of 80° C.±2° C. for about 5 hours. Thus, a hydrous resin (gel 2) was obtained.

This hydrous resin (gel 2) in an amount of 400 parts was minced with a mincer (12VR-400K, manufactured by Iizuka Kogyo K.K., hole diameter of catch basin: 6 mm) at 25° C. for 5 minutes and then dried in a ventilated band drier (135° C., 2.0 m/second; Inoue Kinzoku Kogyo Co., Ltd.), thereby obtaining a dried polymer.

This dried polymer was pulverized with a juicing blender (National MX-X53, manufactured by Matsushita Electric Co., Ltd.), and was controlled to within the particle diameter range of 150 to 710 μm using sieves having sieve-openings of 150 and 710 μm. Then, while stirring 100 parts of this at high speed (a high-speed stirring turbulizer manufactured by Hosokawa Micron Corporation; rotation speed: 2000 rpm), 5.5 parts of a 1% by weight water/methanol mixed solution (weight ratio of water/methanol=60/40) of ethylene glycol diglycidyl ether was added by spraying and mixed, and the resultant was allowed to stand at 140° C. for 30 minutes to achieve heat crosslinking (surface crosslinking). Thus, a granular water-absorbing resin (A2) was obtained.

Production Example 5

Using a continuous mixer (KRCSS, manufactured by Kurimoto, Ltd.) having a diameter of 5 inches and L/D of 10 in which the heat medium temperature of its jacket was preset to 160° C., a mixture in which 50 parts by weight of styrene, 50 parts by weight of maleic anhydride, 350 parts by weight of an ethylene-butene 1 copolymer ("ESPLENE N0377" produced by Sumitomo Chemical Co., Ltd.), 350 parts by weight of a non-crystalline ethylene-propylene copolymer ("UBETAC UT2315" produced by Ube Rexene Corporation), 200 parts by weight of a low molecular weight polypropylene obtained by a thermal degradation method ("VISCOL 660P" produced by Sanyo Chemical Industries, Ltd.), and 0.5 parts by weight of tert-butyl peroxybenzoate were dispersed was fed from a feedstock feeding port of the continuous mixer, and then was subjected to polymerization while controlling the residence time to be 10 minutes. The resulting mixture was made to remove monomers with a twin screw extruder (PCM45, manufactured by Ikegai Ironworks Corp., L/D=50), thereby obtaining a thermoplastic resin (B) having a sea-island structure in the present invention. The melting point of the thermoplastic resin (B) was 105° C.

Example 3

Twenty parts by weight of the granular water-absorbing resin (A2) produced in Production Example 4 and 0.2 parts by weight of the thermoplastic resin (B) synthesized in Production Example 5 were charged into a V-type mixer and mixed for 20 minutes, and then subjected to heat treatment at 150° C. for 15 minutes, thereby obtaining a water-absorbing resin particle (2) whose surface had been coated with the thermoplastic resin (B).

Subsequently, a core-sheath type polyester/polyethylene fiber (the melting point of a lower melting point component was not lower than 50° C. and lower than 150° C.) was fibrillated with a defibrating machine for synthetic fibers (manufactured by Daiwa-Kiko Co., Ltd.) and then subjected to web formation with a sample roller carding machine (ISC-360, manufactured by Intec, INC.). Twenty parts by weight of the water-absorbing resin particles (2) were scattered to 5 parts by weight of the web-like core-sheath type polyester/polyethylene fiber and then subjected to heat treatment at 150° C. for 5 minutes, thereby obtaining an absorber (7).

Comparative Example 5

An absorber (8) was obtained in the same manner except that the thermoplastic resin (B) used in Example 3 was replaced by an acid-modified wax (molecular weight: 1,500, acid value: 60, melting point: 104° C.)

Comparative Example 6

An absorber (9) was obtained in the same manner except that the thermoplastic resin (B) used in Example 3 was replaced by an ethylene vinyl acetate (viscosity: 595 mPa·s, melting point: 92° C.)

Comparative Example 7

An absorber (10) was obtained in the same manner except that the addition amount of the acid-modified wax used in Comparative Example 5 was changed to 1 part by weight.

Comparative Example 8

An absorber (11) was obtained in the same manner except that the amount of the ethylene vinyl acetate used in Comparative Example 6 was changed to 1 part by weight.

The results of water absorption rate, fixation ratio, and shape retention measured for the absorbers (7) to (11) obtained in Example 3 and Comparative Examples 5 to 8 are shown in Table 2.

TABLE 2

| | Absorber | Water absorption rate g/min | Fixation ratio (%) | Shape retention |
|---|---|---|---|---|
| Example 3 | (7) | 18 | 90 | ⊙ |
| Comparative Example 5 | (8) | 17 | 23 | X |
| Comparative Example 6 | (9) | 17 | 37 | X |
| Comparative Example 7 | (10) | 5 | 85 | ○ |
| Comparative Example 8 | (11) | 6 | 89 | △ |

The invention claimed is:

1. A core-shell type water-absorbing resin particle composed of a core layer (P) and a shell layer (Q), wherein the (P) comprises a water-absorbing resin (A), the (Q) comprises a thermoplastic resin (B) having a melting point of 50 to 180° C., and the thermoplastic resin (B) is a polymer having a hydrophobic block comprising a polyolefin, wherein the thermoplastic resin (B) having a melting point of 50 to 180° C. is an alternating block copolymer (G) in which a hydrophobic block of a polyolefin and a block of a hydrophilic polymer are linked via at least one selected from the group consisting of an ester linkage, an amide linkage, an ether linkage and an imide linkage.

2. The water-absorbing resin particle according to claim 1, wherein the volume resistivity of the hydrophilic polymer is $1 \times 10^5$ to $1 \times 10^{11}$ Ω·cm.

3. The water-absorbing resin particle according to claim 1, wherein the alternating block copolymer (G) is a copolymer having a structure represented by the following formula (1):

[Chemical Formula 1]

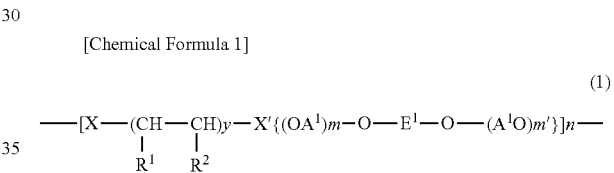

wherein n is an integer of 2 to 50; $R^1$ and $R^2$ are each independently a hydrogen atom or a methyl group, provided that not both of $R^1$ and $R^2$ are methyl groups; y is an integer of 15 to 800; $E^1$ is an alkylene group having 1 to 11 carbon atoms or a phenylene group; $A^1$ is an alkylene group having 2 to 12 carbon atoms and having optionally a halogen atom; m and m' are each independently an integer of 1 to 300; X is a group represented by the following formula (2) or the following formula (3) and X' is a group represented by the following formula (2') or the following formula (3'), provided that when X is a group represented by the formula (2), X' is a group represented by the formula (2'), and when X is a group represented by the formula (3), X' is a group represented by the formula (3'),

[Chemical Formula 2]

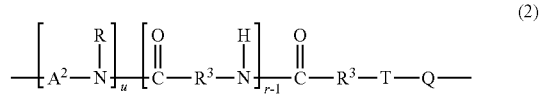

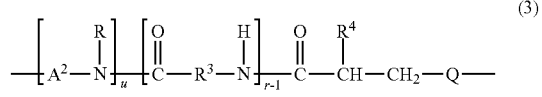

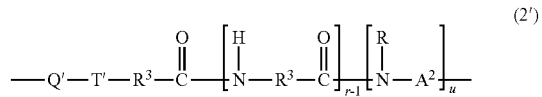

-continued

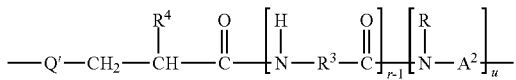

(3')

in the formulae (2), (2'), (3), and (3'), R is a hydrogen atom or an alkyl group having 1 to 4 carbon atoms; $R^3$ is an alkylene group having 1 to 11 carbon atoms; $R^4$ is a hydrogen atom or an alkyl group having 1 to 10 carbon atoms; $A^2$ is an alkylene group having 2 to 12 carbon atoms and having optionally a halogen atom; r is an integer of 1 to 20 and u is 0 or 1; Q is a group represented by the following formula (4); Q' is a group represented by the following formula (4'); T is a group represented by the following formula (5); and T' is a group represented by the following formula (5'),

[Chemical Formula 3]

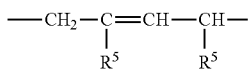

(4)

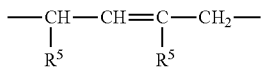

(4')

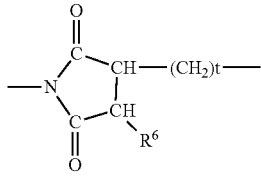

(5)

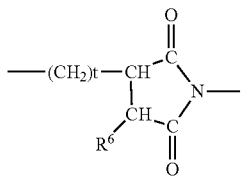

(5')

in the formulae (4), (4'), (5), and (5'), $R^5$ is a hydrogen atom or an alkyl group having 1 to 10 carbon atoms; $R^6$ is a hydrogen atom or a methyl group; t is 1 when $R^6$ is a methyl group and is 0 when $R^6$ is a hydrogen atom.

4. The water-absorbing resin particle according to claim 1, wherein the thermoplastic resin (B) is a thermoplastic resin having a sea-island structure composed of islands formed by more polar domains and the sea formed by less polar domains.

5. The water-absorbing resin particle according to claim 4, wherein the thermoplastic resin (B) is a resin obtained by polymerizing at least one radically polymerizable monomer (E) selected from the group consisting of styrenic compounds, vinyl group-containing carboxylic acids or the derivatives thereof, and (meth)acrylonitrile in a heat-melt kneader in the presence of a low viscosity polyolefin resin (D) and an α-olefin (co)polymer (C) composed of an α-olefin homopolymer (C1) and/or an ethylene/α-olefin copolymer (C2).

6. The water-absorbing resin particle according to claim 5, wherein the weight proportion of the (C), the (D), and the (E) is (C):(D):(E)=100:(30 to 300):(1 to 50).

7. The water-absorbing resin particle according to claim 1, wherein the weight ratio of the thermoplastic resin (B) to the water-absorbing resin (A) is 0.1 to 10% by weight.

8. The water-absorbing resin particle according to claim 1, wherein the thermoplastic resin (B) having a melting point of 50 to 180° C. is a resin containing a low molecular weight polyolefin (H) and/or a plasticizer (I).

9. An absorber in which a water-absorbing resin particle according to claim 1 is fixed to a fibrous base material (F).

10. The absorber according to claim 9, wherein the fixation ratio of the water-absorbing resin particle to the fibrous base material (F) after a vibration test is 50% by weight or more.

11. The absorber according to claim 9, wherein the fibrous base material (F) is one or more selected from the group consisting of a cellulosic fiber, an organic synthetic fiber, and a mixture of a cellulosic fiber and an organic synthetic fiber.

12. The absorber according to claim 9, wherein the organic synthetic fiber is a heat-weldable conjugated fiber of at least one type selected from the group consisting of sheath-core type, eccentric type and parallel type, and comprising a plurality of components differing in melting point wherein the melting point of a low melting point component is 50 to 180° C.

13. An absorbent article using an absorber according to claim 9.

* * * * *